United States Patent [19]
Selby

[11] Patent Number: 5,369,988
[45] Date of Patent: Dec. 6, 1994

[54] COJOINED COLLET

[76] Inventor: Theodore W. Selby, 4800 James Savage Rd., Midland, Mich. 48642

[21] Appl. No.: 816,119

[22] Filed: Dec. 31, 1991

[51] Int. Cl.$^5$ .................. G01N 11/14; F16B 2/06; F16D 1/00
[52] U.S. Cl. .................. 73/54.28; 403/305; 403/314; 279/43.1; 279/43.2
[58] Field of Search .............. 279/43.1, 43.2, 46.4, 279/46.1, 46.2, 47, 48, 100, 101, 46.6; 403/305, 300, 309, 314, 310; 73/54.28, 54.35

[56] References Cited

U.S. PATENT DOCUMENTS

| | | | |
|---|---|---|---|
| 817,588 | 4/1906 | Reising | 403/310 |
| 1,321,264 | 11/1919 | Wagner et al. | 403/300 |
| 3,350,922 | 11/1967 | Kim et al. | 73/54.28 |
| 4,445,365 | 5/1984 | Selby | 73/54.34 |
| 4,645,473 | 2/1987 | Mochizuki | 403/314 |
| 5,129,263 | 7/1992 | Chi | 73/861.38 |

Primary Examiner—Hezron E. Williams
Assistant Examiner—Michael J. Brock
Attorney, Agent, or Firm—Christopher John Rudy

[57] ABSTRACT

Cojoined collet has a center housing with opposing central orifices, each central orifice capable of receiving an externally positioned shaft, and further having a fastener about each opposing orifice, wherein the externally positioned shaft is releasably connectable on a common axis of rotation through the opposing central orifices and can be held fast by the fastener about the central orifice which receives the externally positioned shaft, and it is finely balanced about its intended axis of rotation. It may be coupled in series with a shaft, which may be rigid or flexible, and be embodied for employment in rotating devices, for an example, such as the high-speed simulator-viscometer of U.S. Pat. No. 4,445,365.

20 Claims, 1 Drawing Sheet

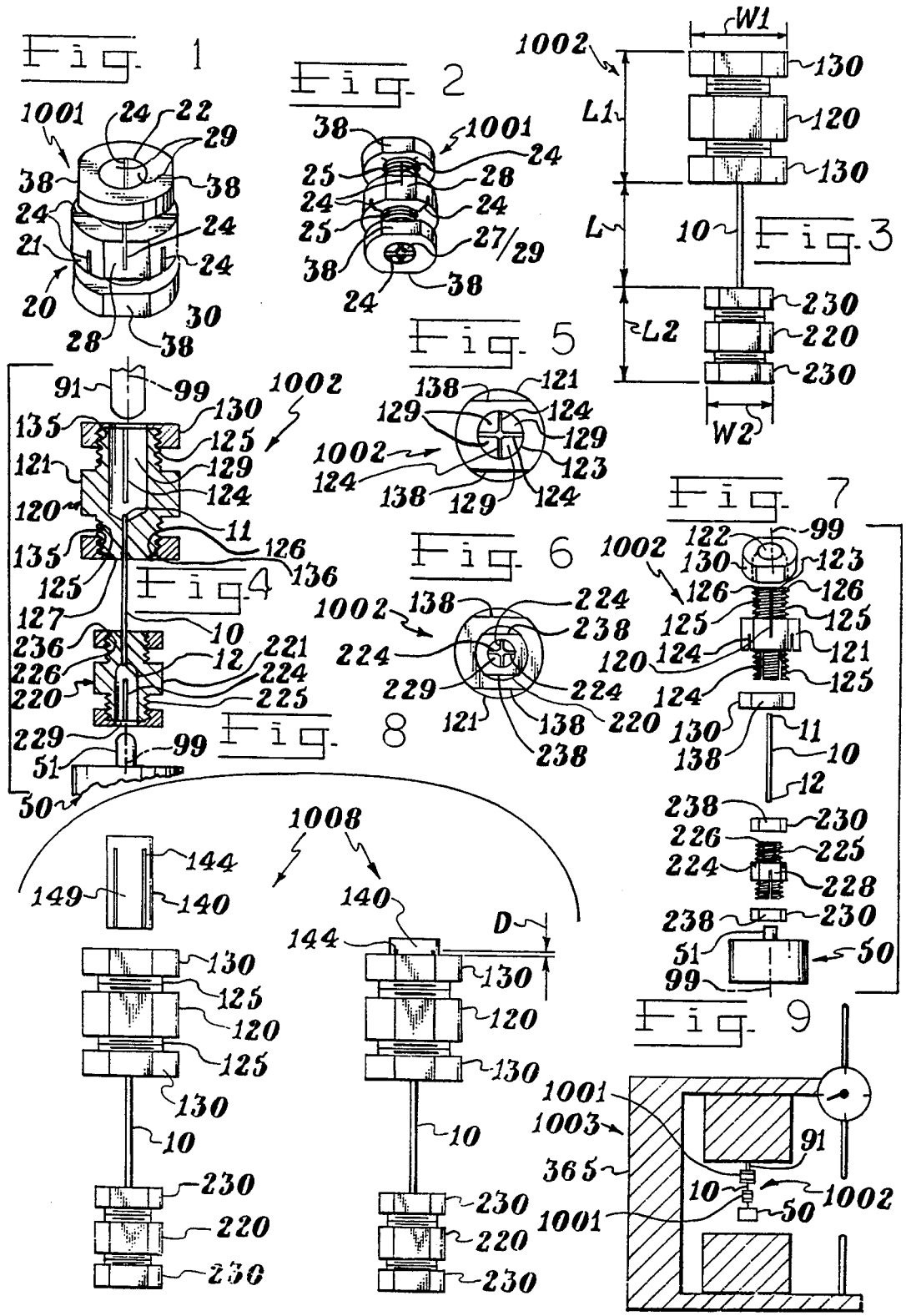

COJOINED COLLET

FIELD

Of concern here is a collet for joining and maintaining prior balance of rotating entities, and devices and uses therewith.

BACKGROUND

Selby, U.S. Pat. No. 4,445,365 (May 1, 1984), discloses a TAPERED BEARING SIMULATOR-VISCOMETER. In it, a flexible drive shaft or cable, coaxially interconnected with a motor above it by a coupling, is fixed upwardly on a cylinder or drum (See e.g., U.S. Pat. No. 3,350,922) that is rotated at high speeds within a liquid-filled cup in order to measure the viscosity of the liquid. See e.g., column 3, lines 36–60, etc. A problem is that that device occasionally becomes inoperable due to breaking of its flexible shaft or cable.

SOME OBJECTS

In general, an object hereof is to overcome or circumvent problems, and fulfill lacks, needs and desires in the art.

In particular, an object is to provide well-balanced collet, which could be used to releasably couple rotating members without loss of the balance which the members have about their common axis of rotation. Another object is to provide such a collet that is itself durable. Another object is to provide for a collet that has such fine balance that it could be coupled in series with other such collets as well. And another object is to provide a way for economical and quick repair of the simulator-viscometer, or similar device, which could be accomplished reliably by persons of limited experience who can be expected to operate the devices.

In fact, an object is to provide a novel manner of joining two rotating elements in a manner avoiding the use of set screws, splines, keys, wedges, tapers, chucks, etc., the choices of prior art. Specifically, although of course not limitingly, an object is to circumvent the aforesaid problem in the operation of the TAPERED BEARING SIMULATOR-VISCOMETER where its motor must turn the flexible shaft at high speeds, which flexible shaft in turn forces rotation of the cylinder or drum within the liquid-filled cup. It is important that the coupling be flexible but that its ends be rigidly mounted to the motor shaft and to the cylinder or drum shaft. In addition, preferably, the coupling device should be balanced so as to avoid transferring imbalance to the rest of the driven coupled members. Moreover, it is important that, should the connecting, e.g., flexible, shaft break, it should be simple and inexpensive to replace.

Further objects hereof are extant as well.

SUMMARY

The present invention provides a cojoined collet. It is finely balanced and releasably attachable, providing generally for close tolerance between it and the rotating objects it can connect before insertion of these objects into its closing orifice pair, closure being accomplishable by applying inwardly directed pressure to its rotationally-balanced-in-coupled-use, typically acutely-angled end and slit end housing, through tightening of its rotationally-balanced collar nuts. It can be present singly or in series with a plurality of connected cojoined collets. A series cojoined collet generally comprises at least:

A) A connecting shaft, which has first and second ends;
B) A first cojoined collet having a center housing with central motor-facing and shaft-facing orifices for receiving a driving (motor) rotor shaft and the first end of the connecting shaft, respectively, and motor-facing and shaft-facing fasteners, and
C) A second cojoined collet having a center housing with central shaft-facing and rotor-facing orifices for receiving the second end of the connecting shaft and a driven rotor shaft, respectively, and shaft-facing and rotor-facing fasteners, wherein the connecting shaft is releasably connectable on a common axis of rotation to each of said collets through the central shaft-facing orifices of said collets and can be held fast by the shaft-facing fasteners of said collets.

Also provided is, in a liquid viscosity rotating testing device having a flexible shaft or cable attachable coaxially to a motor rotor and to a driven rotor, especially a simulator-viscometer according to U.S. Pat. No. 4,445,365, the improvement which comprises the flexible shaft or cable being a series cojoined collet flexible shaft. In other aspects, methods of using of the aforesaid in such rotating devices are provided.

The invention solves significant problems and fulfills needs in the art, to include those mentioned in the background hereof. To meet the aforementioned set of needs, is provided in one embodiment, for example, a twin collet poised back-to-back having an opening in its one end to accommodate a shaft of one size and an opening in its other end to accommodate a shaft of a different size, wherein no fastening method other than a slight squeezing of the collet fingers by a turning of the collet nut was required at either end of the cojoined collet in order to have a firm grip on the shafts and a balanced coupling. It provides a novel means of joining two rotating elements in a manner which can, and preferably does, avoid the use of set screws, splines, keys, wedges, tapers, chucks, etc., the choices of prior art. In series, it circumvents the aforementioned problems in the TAPERED BEARING SIMULATOR-VISCOMETER, for example, and fulfills objects concerning it, and thus, it provides for a flexible connecting shaft, the ends of which can be rigidly mounted to device motor and drum shafts, which too is balanced so as to avoid transferring imbalance to the rest of the driven coupled members, and moreover, should the connecting, e.g., flexible, shaft break, it is simple and inexpensive to replace, even by the persons of limited experience. By satisfying objects such as aforesaid, it provides a truly remarkable advance in the art. Thus, many advantages attend it, and so, it enjoys commercial success.

DRAWINGS

The drawings form part of the specification hereof.

FIG. 1 is a top perspective view, from a top vantage point, of a cojoined collet of the present invention.

FIG. 2 is a bottom perspective view of the same collet.

FIG. 3 is a side view of a series cojoined collet shaft.

FIG. 4 is a cut-away side view of the same series collet.

FIG. 5 is a top view of the same series collet.

FIG. 6 is a bottom view of the same series collet.

FIG. 7 is an exploded side view of the same series article and drum.

FIG. 8 are partially exploded and assembled side views of another similar collet but further emphasizing a collet bushing.

FIG. 9 is a side view of a cojoined collet flexible shaft article assembled with a modified simulator-viscometer of Selby.

FURTHER DETAIL

Those patents mentioned herein are incorporated by reference.

The term cojoined is employed herein; this lexicon refers to the collet of the present invention, which need not be infinitely symmetrical, nor if in series need the cojoined collet components be of the same size or overall shape. What is highly important is that the cojoined collets hereof be rotationally balanced when coupled for use in rotating devices.

In further reference to the drawings, in which like numerals refer to like features, is noted the following:

Single cojoined collet 1001 is depicted in FIGS. 1 and 2. It is shown having housing 21, the extremities of which are generally beveled, first orifice 22, second orifice 23, slits 24, male threads 25, with which female threads (not shown) inside rotationally balanced internally beveled nuts 30 register, housing face 27, and tightening faces 28 and 38. Tightening of nuts 30 squeezes extremities, e.g., fingers 29, of housing 21 in, accommodated by slits 24, around shaft inserted into orifice 22 and/or 23. Although the orifices are depicted as being circular, that need not be, but preferably is, the case, as inserted shaft(s) need not be, but preferably are, cylindrical. Although not preferred, shims, keys, etc., may be employed. Bushings may be employed. The orifice also may be, for example, tapered, cylindrically-arced with one or more chords therein, triangular, rectangular, square, and so forth and the like. However, the cojoined collet advantageously has generally cylindrical orifices for accommodation of cylindrical shafts. Importantly, the cojoined collet is finely balanced when coupled for use in a rotating device about axis 99.

Series cojoined collet shaft is depicted as a double cojoined collet shaft 1002 in FIGS. 3–8 and 9, but there could be more than two cojoined collets of the invention connected in a series. The double cojoined collet shaft, in general, includes the aforesummarized connecting shaft, and first and second cojoined collets. The connecting shaft may be rigid or flexible, although a flexible shaft can be employed to great advantage.

Accordingly, connecting shaft 10 is made to be flexible and has first and second ends 11 and 12. Preferably, any connecting shaft is cylindrical. The connecting shaft can be any suitable size so long as it is generally strong enough to transmit an applied rotational force, e.g., as encountered in high-speed viscosity testing. It thus can be any suitable length and width. The flexible connecting shaft is made of suitable material, as aforesaid, but generally being flexible. For instance, flexible shaft 10, strong enough to transmit rotational force in use in high-speed rotating testing device 365, can be of a size to include those with a length about from one to four inches and a width, e.g., diameter, about from 1/40 to 1/20 of an inch, and can be made of a suitably resilient spring-type wire such as, for example, of a #20-gage (0.035-inch diameter) steel piano wire (Schlaff Co.) cut to about two inches in length, with its ends rounded somewhat.

The connecting shaft is releasably connectable to each of the first and second collets (collet components) through the central shaft-facing orifices of these components, generally on a common axis of rotation. This common axis of rotation is an axis of rotation of the cojoined collet during its contemplated rotating use, which is generally shared by the first and second collet components, as well as the flexible shaft. The connecting shaft can be held fast by the shaft-facing fasteners of the first and second collets. Preferably, flexible shaft 10 is held fast leaving approximately one inch of it bridging the first and second collet components of the cojoined collet flexible shaft hereof at length L.

First cojoined collet 120 has center housing 121 with central motor-facing and shaft-facing orifices 122 and 123, respectively, for receiving motor rotor shaft 91 and first end of connecting (flexible) shaft 11. Preferably, these orifices are both circular, with centers at center of common axis of rotation 99. It also has the motor-facing and shaft-facing fasteners. At least the shaft-facing fastener can transmit pressure for holding the flexible shaft fast, and preferably, also the motor-facing fastener can transmit pressure for holding the motor rotor shaft fast, especially if it is cylindrical. Thus, preferably, motor rotor shaft 91 is cylindrical, but slotted-keyed and/or flat-sided motor shafts, desirably with the motor-facing orifice in suitable registry therewith, among other combinations, are possible. One suitable way of providing for such pressure transmission is with housing 121 having slits 124 cut through to provide gaps, say, of about 1/50 to 1/40 of an inch or so, for a distance along it to define fingers 129, and male threads 125 about the outside of the housing there, and in conjunction, providing both a beveled or tapered portion 126 near the ends and suitable nuts 130, correspondingly internally reverse beveled or tapered 136, to screw on by female threads 135 and squeeze the housing tight around the shaft in the central orifice of the housing. For example, the bevel 126 can be a 45-degree bevel, and the reverse bevel 136 can be a 40-degree bevel. The shaft-facing part of the first collet housing may have a built-in washer or bushing for accommodation of the flexible shaft, which is preferably built-in as face 127 adjacent the shaft-facing end of the housing. The shaft-facing orifice 123 runs through this face. The orifices may be in communication, especially along the direction of the common axis of rotation 99. Tightening faces 128 and 138 may be present on the first collet housing and nuts. The first collet can be any suitable size and is most suitably balanced for its smooth rotation about this axis. For instance, the first collet can be a size included within sizes about from one inch to 1½ of an inch in length L1 and ½ to ¾ of an inch in width W1, and for example, first collet 120 can actually have an about 0.685-inch shaft-facing face 127, an about 0.750-inch nut 130 width W1 and an about 1.063-inch length L1 parallel with axis 99 when tightened.

Second cojoined collet 220 also has the center housing with central shaft-facing and rotor-facing orifices for respectively receiving the second end of the flexible connecting shaft 10 and driven rotor shaft, say, of a drum of a rotating testing device, e.g., of a drum as of or modified from U.S. Pat. No. 4,445,365, and for accepting the shaft-facing and rotor-facing fasteners. Like the first collet component, at least the shaft-facing fastener can transmit pressure for holding the flexible shaft fast, and it is preferably similar in construction to the first, as aforesaid, excepting that it advantageously may be smaller or larger in certain situations, in the case here, it is smaller. Accordingly, second collet 220 has center housing 221, central rotor-facing orifice 223 and shaft-facing orifices 222, preferably both circular, also with centers at center of common axis of rotation 99. Housing 221 also has slits 224 and male threads 225 with a beveled or tapered portion 226 e.g., at a 45-degree bevel, and fingers 229. Also, suitable nuts 230, correspondingly internally reverse beveled or tapered 236, e.g., at a 40-degree bevel, with female threads 235, are provided. Also, face 227 is adjacent the shaft-facing end of the housing; shaft-facing orifice 223 runs through this face, and the orifices may be in communication, especially along the direction of the common axis of rotation 99. Tightening faces 228 and 238 may be present on the second collet housing and nuts. The second collet also is most suitably balanced for its smooth rotation about this axis. The second collet, for instance, can be of a size included within sizes about from $\frac{3}{4}$ to $1\frac{1}{4}$ of an inch in length L2 and about from $\frac{1}{4}$ to $\frac{3}{4}$ of inch in width W2, and for example, second collet 220 can actually have an about 0.435-inch shaft-facing face 227, an about 0.50-inch nut 230 width W2 and an about 0.840-inch length L2 parallel with axis 99 when tightened.

The first and/or second collets can be provided with a collet bushing, or another suitable spacer such as shims, to accommodate the receipt of various sized shafts. The collet bushing can be made to be squeezed from a suitable fastener to transmit pressure through it to the shaft and can be made from a softer material than the housing of the first collet or can be made of the same material as the first collet housing. For instance, first collet 120 can be provided with bushing 140, e.g., of stainless steel, with slits 144 cut up a suitable share of its length, providing fingers 149. Preferably, any slits are cut so that they extend into the appropriate, e.g., first, cojoined collet housing, say, extending into the motor-facing orifice, with a minimum amount, e.g., at least about 1 mm or so, in distance D extending above the fastener (nut 130) face.

Drum 50, having shaft 51, is for viscosity testing.

In FIG. 9 is shown viscosity testing device 1003 hereof. It has double cojoined collet shaft 1002 of two cojoined collets 1001, flexible shaft 10 with drum 50 as in FIGS. 1–8, and simulator-viscometer part 365 modified from U.S. Pat. No. 4,445,365 with motor shaft 91.

The cojoined collet, to include the first and second, third, etc., cojoined collet components, collet bushing(s), drum, and even the connecting shaft, can be made of a suitable material such as metal and/or engineering thermoplastic components. For example, the aforementioned first and second cojoined collet components, the slit bushing, and the viscosity testing drum can be made of #303 stainless steel, which is forged or rolled, drilled, slit by cutting, threaded by tap and die, milled, hardened, and polished, as may be appropriate.

The manufacturing must provide the critically-required balance of the cojoined collet and assembled series cojoined collet shaft hereof. Accordingly, for example, any slits are preferably symmetrically arranged such as in planes which intersect normal to one another at a line along axis 99. Slits in the first and second collet components may be in pairs of such intersecting planes, with one normal set of intersecting planes being at a 45-degree angle to the other set of intersecting planes.

The cojoined collets are advantageously designed so that very close tolerances are achieved with any shafts they may connect before they are fastened. Fine balance is of critical concern.

Articles and devices of the present invention are available from TANNAS CO., Midland, Mich. They enjoy commercial success.

Numerous further advantages attend this invention.

CONCLUSION

The present invention is thus provided. Numerous adaptations can be effected within the spirit of the invention, the asserted scope of which is particularly pointed out in the claims hereof.

What is claimed is:

1. An article of manufacture that is a series cojoined collet shaft comprising the following components:
   A) a plurality of cojoined collets, each having:
      1) a housing with a main axis of rotation having:
         a) a central portion,
         b) two elongate, opposing portions extending from the central portion along the main axis of rotation, each of the two elongate, opposing portions having a central orifice centered on the main axis of rotation so that there are two central orifices centered on the main axis of rotation per housing, and each of these two central orifices being capable of receiving an externally positioned shaft so that there can be received two externally positioned shafts per housing through these two central orifices, one externally positioned shaft per each of these central orifices,
         c) straight shank male threads on the outside of both elongate, opposing portions of the housing, directed for screwing along the main axis of rotation,
         d) a beveled or tapered portion, without threads, at ends of both elongate portions, to accept guiding pressure of a nut for closure,
         e) a plurality of slits perforating the male threads and housing to its central portion, extending substantially beyond the beveled or tapered portion toward the central portion, each set communicating with one of the central orifices, to form a plurality of elongate fingers, and further
      2) a fastener about each opposing central orifice, which is the nut for closure having:
         a) straight, internal, female threads corresponding to the male threads, and
         b) an internal reverse bevel or taper, without threads, closely corresponding to the beveled or tapered portion of the elongate, fingered portion of the housing so as to exert desired pressure on the beveled or tapered area and squeeze tight the externally positioned shaft in the central orifice,
      each nut able to be screwed on to squeeze the fingers inwardly through action of the bevel or taper only;
   B) wherein at least one of the externally positioned shafts is a connecting shaft with first and second ends, connected to:
      1) a first cojoined collet selected from among the plurality of the cojoined collet components, and
      2) a second cojoined collet selected from among the plurality of the cojoined collet components,
   and wherein each externally positioned shaft is releasably connectable on a common axis of rotation along the main axis of rotation through the opposing central orifices and can be releasably held fast by pressure of the nut fastener acting on the beveled or tapered surfaces about the central orifice which receives the externally positioned shaft; the series cojoined collet shaft is rotationally balanced about the common axis of rotation, and the plurality of cojoined collets are releasably connected by the connecting shaft(s).

2. The article of claim 1, wherein:
the connecting shaft with first and second ends is a wire;
the first SIAMESE collet central orifices are driving-rotor-facing and connecting shaft-facing orifices for receiving a driving rotor shaft and the first end of the connecting shaft, respectively, wherein the shaft-facing orifice is circular and of a smaller diameter than the driving-rotor-facing orifice;
the second SIAMESE collet central orifices are connecting shaft-facing and driven-rotor-facing orifices for receiving the second end of the connecting shaft and a driven rotor shaft, respectively, wherein the shaft-facing orifice is circular and of a smaller diameter than the driven-rotor-facing orifice, and
there are two opposing pairs of slits in communication with each central orifice per housing, parallel to the main axis of rotation.

3. The article of claim 2, wherein the housings are of stainless steel, and the connecting shaft is of steel wire.

4. The article of claim 3, wherein the central orifices of each cojoined collet are in communication within the collet along the common axis of rotation; the first and second cojoined collets differ in size of their housings from each other, and the connecting shaft is flexible and about from 1/40 to 1/20 of an inch in diameter.

5. The article of claim 2, wherein the connecting shaft is a flexible connecting shaft.

6. The article of claim 5, which is a double cojoined collet shaft, which further comprises a drum releasably attached to an external shaft inserted in the driven-rotor-facing orifice of the second cojoined collet.

7. The article of claim 5, which is a double cojoined collet shaft, which further comprises a drum releasably attached to an external shaft inserted in the driven-rotor-facing orifice of the second cojoined collet.

8. The article of claim 1, further comprising a collet bushing.

9. The article of claim 1, wherein the connecting shaft is a flexible connecting shaft.

10. In a liquid viscosity rotating testing device having a flexible shaft or cable attachable coaxially to a motor rotor and to a driven rotor, the improvement which comprises the flexible shaft or cable being a series cojoined collet flexible shaft having the following components:

A) a plurality of cojoined collets, each having:
   1) a housing with a main axis of rotation having:
      a) a central portion,
      b) two elongate, opposing portions extending from the central portion along the main axis of rotation, each of the two elongate, opposing portions having a central orifice centered on the main axis of rotation so that there are two central orifices centered on the main axis of rotation per housing, and each of these two central orifices being capable of receiving an externally positioned shaft so that there can be received two externally positioned shafts per housing through these two central orifices, one externally positioned shaft per each of these central orifices,
      c) straight shank male threads on the outside of both elongate, opposing portions of the housing, directed for screwing along the main axis of rotation,
      d) a beveled or tapered portion, without threads, at ends of both elongate portions, to accept guiding pressure of a nut for closure,
      e) a plurality of slits perforating the male threads and housing to its central portion, extending substantially beyond the beveled or tapered portion toward the central portion, each set communicating with one of the central orifices, to form a plurality of elongate fingers, and further
   2) a fastener about each opposing central orifice, which is the nut for closure having:
      a) straight, internal, female threads corresponding to the male threads, and
      b) an internal reverse bevel or taper, without threads, closely corresponding to the beveled or tapered portion of the elongate, fingered portion of the housing so as to exert desired pressure on the beveled or tapered area and squeeze tight the externally positioned shaft in the central orifice,
   each nut able to be screwed on to squeeze the fingers inwardly through action of the bevel or taper only;

B) wherein at least one of the externally positioned shafts is a connecting shaft with first and second ends, connected to:
   1) a first cojoined collet selected from among the plurality of the cojoined collet components, and
   2) a second cojoined collet selected from among the plurality of the cojoined collet components,
and wherein each externally positioned shaft is releasably connectable on a common axis of rotation along the main axis of rotation through the opposing central orifices and can be releasably held fast by pressure of the nut fastener acting on the beveled or tapered surfaces about the central orifice which receives the externally positioned shaft; the series cojoined collet shaft is rotationally balanced about the common axis of rotation, and the plurality of cojoined collets are releasably connected by the connecting shaft(s).

11. The device of claim 10, wherein the liquid viscosity rotating testing device is a simulator-viscometer which is an elevated temperature variable-gap rotational viscometer having:
a thermally-conductive stator block embedded in thermal insulation and having an inverted frusto-conical vertical bore, an inlet passage for admitting sample liquid axially into the bore at its bottom, and an overflow passage for sample liquid to leave the bore at its upper end;
a thermal sensor recessed in the block;
an element for heating the block responsive to the sensor;
a matching rotor extending axially downward into the stator bore to define therebetween a thin annular measuring gap, the rotor having a flexible drive shaft extending axially upward from it;

a multi-speed synchronous AC motor coaxial with and directly driving the shaft;

a turntable fixed to and supporting the motor and having a torque arm projecting therefrom, the turntable being supported on a low-friction bearing resting on a cantilevered platform vertically adjustable by a fine screw, and being restricted in rotation to a limited arc, and a stationary force-measuring element opposing movement of the torque arm.

12. The device of claim 11, wherein the series cojoined collet flexible shaft is a double cojoined collet flexible shaft wherein:

the connecting shaft with first and second ends is a flexible steel wire;

the first cojoined collet central orifices are driving-rotor-facing and connecting shaft-facing orifices for receiving a driving rotor shaft and the first end of the connecting shaft, respectively, wherein the shaft-facing orifice is circular and of a smaller diameter than the driving-rotor-facing orifice; the central portion of the housing of is collet has opposing tightening faces thereon, and the housing is stainless steel;

the second cojoined collet central orifices are connecting shaft-facing and driven-rotor-facing orifices for receiving the second end of the connecting shaft and a driven rotor shaft, respectively, wherein the shaft-facing orifice is circular and of a smaller diameter than the driven-rotor-facing orifice; the central portion of the housing of this collet has opposing tightening faces thereon, and the housing is of a stainless steel, and there are two opposing pairs of slits in communication with each central orifice per housing, parallel to the main axis of rotation, and which device also has a viscosity testing drum releasably attached as part of an external shaft inserted in the driven-rotor-facing orifice of the second cojoined collet.

13. The device of claim 12, wherein the double cojoined collet flexible shaft further comprises a bushing in the driving-rotor-facing orifice of the first cojoined collet.

14. The device of claim 12, wherein the thin annular measuring gap of the liquid viscosity rotating testing device can gather any particles in the test fluid likely to jam in the gap from the rotor having in a surface thereof matching with the stator block to form the annular measuring gap incised areas radially symmetrical and extending the full axial length of the rotor, each incised area having axially therein a fillet constituting a pocket-like depression along its trailing edge to entrap particles, the depth of the fillet being small relative to the radius of the rotor, and in which each incised area is parallel to the rotor axis and the face of each fillet in the rotor recedes gradually inward most of its width and returns sharply outward over the last part of its width to the full diameter of the rotor.

15. The device of claim 14, wherein the double cojoined collet flexible shaft further comprises a bushing in the driving-rotor-facing orifice of the first cojoined collet.

16. A cojoined collet comprising:
A) a housing with a main axis of rotation having:
1) a central portion,
2) two elongate, opposing portions extending from the central portion along the main axis of rotation, each having a central orifice centered on the main axis of rotation and capable of receiving an externally positioned shaft,
3) straight shank male threads on the outside of both elongate, opposing portions of the housing, directed for screwing along the main axis of rotation,
4) a beveled or tapered portion, without threads, at ends of both elongate portions, to accept guiding pressure of a nut for closure,
5) a plurality of slits perforating the male threads and housing to its central portion, extending substantially beyond the beveled or tapered portion toward the central portion, each communicating with one of the central orifices, to form a plurality of elongate fingers, and further
B) a fastener about each opposing central orifice, which is the nut for closure having:
1) straight, internal, female threads corresponding to the male threads, and
2) an internal reverse bevel or taper, without threads, closely corresponding to the beveled or tapered portion of the elongate, fingered portion of the housing so as to exert desired pressure on the beveled or tapered area and squeeze tight the externally positioned shaft in the central orifice, wherein each nut is able to be screwed on to squeeze the fingers inwardly and tightly around a shaft or bushing in the central orifice through action of the bevel or taper only; two externally positioned shafts are releasably connectable on the main axis of rotation through respective opposing central orifices and can be releasably held fast by the nut fastener about the central orifice which receives the externally positioned shaft, and the cojoined collet is rotationally balanced about the main axis of rotation.

17. The cojoined collet of claim 16, wherein at least one central orifice can accommodate a wire shaft without use of a bushing.

18. The cojoined collet of claim 17, wherein the opposing central orifices are of different cross-sectional dimensions.

19. The cojoined collet of claim 18, wherein the housing is stainless steel.

20. The cojoined collet of claim 18, wherein there are two sets of opposing slits about each central orifice, parallel to the main axis of rotation.

* * * * *

UNITED STATES PATENT AND TRADEMARK OFFICE
CERTIFICATE OF CORRECTION

PATENT NO. : 5,369,988
DATED : December 6, 1994
INVENTOR(S) : Theodore W. Selby

It is certified that error appears in the above-indentified patent and that said Letters Patent is hereby corrected as shown below:

In the drawings, in Figure 8, delete "1008" and insert therefor -- 1002 --.

At column 5, line 7, after "226" insert a comma.

In claim 2, line 4 thereof, i.e., at column 7, line 13, delete "SIAMESE" and insert therefor -- cojoined --.

In claim 2, line 10 thereof, i.e., at column 7, line 19, delete "SIAMESE" and insert therefor -- cojoined --.

Signed and Sealed this

Twentieth Day of August, 1996

Attest:

BRUCE LEHMAN

*Attesting Officer*   *Commissioner of Patents and Trademarks*